United States Patent [19]

Hanotier et al.

[11] 4,380,662
[45] Apr. 19, 1983

[54] PROCESS FOR THE PURIFICATION OF TEREPHTHALIC ACID

[75] Inventors: Jacques D. V. Hanotier, Lasne Chapelle St. Lambert; Jacques F. Dauby, Groot-Bijgaarden, both of Belgium

[73] Assignee: Labofina, S.A., Brussels, Belgium

[21] Appl. No.: 243,703

[22] Filed: Mar. 16, 1981

[51] Int. Cl.$^3$ .............................................. C07C 51/42
[52] U.S. Cl. .................................................. 562/486
[58] Field of Search ........................................ 562/486

[56] References Cited

U.S. PATENT DOCUMENTS 2,838,565  6/1958  Heath et al. ........................ 562/486
3,452,088  6/1969  Olsen et al. ......................... 562/486
3,505,398  4/1970  Baldwin ............................... 562/486

Primary Examiner—Alan Siegel

[57] ABSTRACT

Disclosed is a process for the purification of a crude terephthalic acid product contaminated with up to 10% by weight of partially oxidized impurities including p-toluic acid and 4-carboxybenzaldehyde, comprising the steps of dissolving the crude product in water by heating up to a temperature at least about 5° C. higher than necessary for having the resulting solution saturated with terephthalic acid; cooling the resulting solution down to a temperature not lower than about 185° C. to precipitate purified crystals; recovering the purified crystals by solid-liquid separation at a temperature not lower than that used for the precipitation of the purified crystals; and washing the recovered crystals by contacting with water at a temperature which is at least as high as the temperature of the recovery step.

11 Claims, No Drawings

PROCESS FOR THE PURIFICATION OF TEREPHTHALIC ACID

BACKGROUND OF THE INVENTION

The present invention relates to a process for the purification of impure terephthalic acid produced by oxidation with air of p-xylene and/or the partially oxidized derivatives thereof, such as p-tolualdehyde and p-toluic acid. More particularly, it relates to the removal of such impurities as p-toluic acid and 4-carboxybenzaldehyde by crystallization at sufficiently high temperatures, without resorting to any chemical purification procedure such as post-oxidation, hydrogenation or decarbonylation.

It is a well known fact that terephthalic acid used as a starting material for the manufacture of polyester fibers and films must achieve a high degree of purity, since the presence of contaminants, even in minute amounts, during the polycondensation of terephthalic acid with ethylene glycol has pernicious consequences upon the quality of the resulting resin. For instance, monocarboxylic acid oxidation intermediates, such as p-toluic acid and/or 4-carboxybenzaldehyde, may react with ethylene glycol when present in the polycondensation reaction mixture and therefore act as a chain stopper, with the consequence that the melting point and strength of the resulting polyester may be substantially and undesirably lowered.

As a matter of fact, most processes disclosed in the prior art for the purification of terephthalic acid to be used for the manufacture of polyester fibers are directed to the removal therefrom of p-toluic acid and/or 4-carboxybenzaldehyde. To summarize the enormous amount of published material devoted to this commercially important problem, it can be stated that p-toluic acid is generally removed through controlled recrystallization of terephthalic acid under well defined conditions, whereas 4-carboxybenzadlehyde must be chemically transformed into another compound which is more easily separable from terephthalic acid by physical means. Thus, for example, 4-carboxybenzaldehyde is converted to p-toluic acid and/or p-methylolbenzoic acid through hydrogenation or benzoic acid through decarbonylation. For instance, in British Pat. No. 1,152,575 there is described a process which comprises treating an aqueous solution of impure terephthalic acid at high temperature (450°-600° F. or 232°-316° C.) in the presence of hydrogen with a platinum-charcoal hydrogenation catalyst to effect reduction of 4-carboxybenzaldehyde and recovering fiber-grade terephthalic acid by crystallization from the solution by controlled rate evaporation of water in a cascade of several crystallizers operated at decreasing temperatures. Terephthalic acid containing as low as 25 ppm of residual 4-carboxybenzaldehyde can be obtained by this method.

In order to be purified efficiently to the fiber-grade, the crude terephthalic acid used as starting material in the procedure described hereabove must have a purity of at least 99% by weight, preferably 99.5%, with 4-carboxybenzaldehyde as the principal impurity. In fact, this procedure was especially designed for the purification of crude terephthalic acid obtained by liquid-phase oxidation of p-xylene at high temperature and pressure in the presence of acetic acid as a solvent and a bromine-containing compound as a promoter. Under such vigorous conditions, high reaction rates and high conversions are achieved with the advantageous results that terephthalic acid precursors such as p-toluic acid and 4-carboxylbenzaldehyde are present at relatively low concentrations in the reaction medium where terephthalic acid crystals are growing and therefore show little tendency to become occluded therein. However, this advantage is to some extent counterbalanced by the fact that the severity of the conditions used also results in serious corrosion problems and in partial burning of the acetic acid solvent. Consequently, combining a high-severity oxidation process with a relatively cumbersome purification procedure to remove as little as 0.5% of impurities increases more and more the production costs of fiber-grade terephthalic acid, inasmuch as energy and chemicals are becoming more expensive.

For this reason, several modifications of that oxidation process have recently been proposed, according to which the severity of the operating conditions is increased still more to obtain directly, i.e., without resorting to complicated and costly purification procedures, a terephthalic acid product which contains 300 to 1000 ppm of 4-carboxybenzaldehyde (medium-purity terephthalic acid) but which is still claimed to be suitable for the manufacture of polyester fibers. However, the increased severity of these modified processes results in increased corrosion problems and in increasing combustion rates of acetic acid, with the consequences that that which is gained on one side is at least partly lost on the other side.

Another approach to solve the problem is to reduce the production costs of crude terephthalic acid. As shown recently in U.S. patent application Ser. No. 030,054, it is possible to oxidize p-xylene into terephthalic acid with good yield and practical rates while using mild conditions and substituting water for acetic acid as a solvent. Combining this oxidation procedure with a purification method of the type mentioned above should result, at first glance, in substantial cuts in the production costs of fiber-grade terephthalic acid, especially because water could be used as the same solvent for both stages. However, in this water-diluted oxidation system, the concentration of p-toluic acid must inherently be maintained sufficiently high to allow the reaction to take place without a brominated promoter, with the result that substantial amounts of intermediate products become occluded into the crystals of terephthalic acid growing in the medium. Actually, these crystals may contain as much as 3-5% by weight of p-toluic acid and 2-2.5% of 4-carboxybenzaldehyde, and therefore they do not satisfy the conditions required for purification by the hydrogenation procedure described in the British patent referred to hereinabove.

To solve this other problem, it has been proposed in U.S. patent application Ser. No. 143,141 to modify the hydrogenation procedure by adding small amounts of various transition metals into the hydrogenation medium. In this way, the 4-carboxybenzaldehyde level can surprisingly be reduced from, e.g., 2%, down to less than 20 ppm in one step. However, since the resulting product may contain more than 5% of p-toluic acid, it is not possible to achieve the purification thereof by any crystallization procedure disclosed in the prior art. In order to do this, it would be necessary to first submit the hydrogenated product to some preliminary leaching, digestion or extraction with water at high temperature, which would result in additional processing costs. So, here again, in the converse manner, that which is gained on one side is partly lost on the other.

SUMMARY OF THE INVENTION

It is therefore an object of the present invention to provide an improved process for the purification of terephthalic acid.

It is one principal object of the present invention to provide a simple and economical process for the purification of crude terephthalic acid containing substantial amounts of partially-oxidized impurities.

It is another object of this invention to achieve this purification by resorting only to physical means.

Still another object of the invention is to provide such a process wherein the partially-oxidized impurities can easily be recovered for further oxidation into additional terephthalic acid.

In accomplishing the foregoing objects, there has been provided according to the present invention a process for the purification of a crude terephthalic acid product contaminated with up to 10% by weight of partially-oxidized impurities comprising p-toluic acid and 4-carboxybenzaldehyde, which comprises the steps of dissolving the crude product in water by heating up to a temperature at least about 5° C. higher than the temperature necessary for having the resulting solution saturated with terephthalic acid, cooling the resulting solution down to a temperature not lower than about 185° C. to precipitate purified crystals, recovering the crystals by solid-liquid separation at a temperature not lower than that used for the crystallization, and washing the separated crystals by contacting them with water at a temperature which is at least the same as the temperature used in the crystallization and separating steps.

Further objects, features and advantages of the present invention will become apparent from the detailed description of preferred embodiments which follows.

DETAILED DESCRIPTION OF PREFERRED EMBODIMENTS

The process of the present invention can be applied with advantage to the purification of impure terephthalic acid contaminated with 4-carboxybenzaldehyde, p-toluic acid or other impurities more soluble in water at high temperature than terephthalic acid itself. For instance, it can be applied to the purification of terephthalic acid obtained by disproportionation of potassium benzoate. If some benzaldehyde is present in the benzoic acid subjected to disproportionation, it may be transformed into 4-carboxybenzaldehyde which would contaminate the final terephthalic acid product. Similarly, 4-carboxybenzaldehyde is always present in terephthalic acid produced by the oxidation of p-tolualdehyde, either in acetic acid or in an aqueous medium. Furthermore, it is also present together with various amounts of p-toluic acid in terephthalic acid obtained from p-xylene through any oxidation process, e.g., nitric acid oxidation or, more commonly, liquid-phase oxidation with air.

Typically, however, the process of the present invention is especially useful for the purification of terephthalic acid produced by oxidation of p-xylene and/or p-toluic acid with air in an aqueous medium. Such a process has been described for instance in U.S. patent application Ser. No. 186,101, the disclosure of which is hereby incorporated by reference. It comprises oxidizing p-xylene in aqueous medium at a temperature of 140° to 220° C. and recovering crystals of crude terephthalic acid as a slurry in pure water from the bottom of a sedimentation column operated at sufficiently high temperature. As already mentioned, the crude terephthalic acid recovered by this method typically contains about 2.0–2.5% by weight of 4-carboxybenzaldehyde and about 3.0–5.0% of p-toluic acid, and in this form it cannot be purified by the methods disclosed in the prior art unless it is submitted to some preliminary purification treatment, such as a digestion in water at high temperature to bring its purity up to the 99.5% level generally required by those known methods.

According to one embodiment of the present invention, however, the slurry of impure terephthalic acid as it is recovered from the bottom of the sedimentation column can be used directly as a feed. It needs only to be heated up to a temperature sufficiently high to bring about complete solubilization of the solid material present therein. The minimum temperature to be applied is that at which the resulting solution is saturated with terephthalic acid. It can be calculated by application of the following empirical formula: $T = 57.15 \log [TPA] + 184.9$, where T is temperature in °C. and [TPA] is the concentration of terephthalic acid present in parts by weight per 100 parts of water. In practice, however, it is preferred to work at a temperature which is at least 5° C. higher than this minimum value, in order to avoid technical troubles which might result from premature crystallization of terephthalic acid in the transfer lines and other parts of the equipment.

As will be shown hereinbelow, the efficiency of the purification achieved by the process of the present invention is dependent only to a relatively small degree on the concentration in the solution of the material to be purified. Consequently, there is no advantage in dissolving the latter in a large volume of water, which would charge the process with additional and useless operating and capital investment costs. The lower the concentration of dissolved terephthalic acid, the lower is the proportion thereof recovered as purified crystals, and the higher would be the proportion of material to be reprocessed from the mother liquor. On the other hand, the logarithmic dependence of T upon [TPA], as shown in the above formula, implies that the temperature to be applied increases rapidly as the solid to be dissolved becomes a more concentrated slurry. Accordingly, there is likewise no advantage in using such high concentrations that the temperatures to be applied would result in excessive pressures and tremendous corrosion problems. In practice, concentrations of terephthalic acid of between about 5 and 50 parts per 100 parts of water are used with advantage, preferably between about 10 and 30 parts, which corresponds to a solubilization temperature T of between about 242° and 269° C., respectively, as calculated by the formula given hereabove. The working temperature will therefore be comprised between about 247° C. and 275° C. The vapor pressures developed by water at these temperatures amounts to between about 37 and 59 atmospheres.

Once the solid terephthalic acid material to be purified has been completely dissolved in water by appropriate heating, it is then recrystallized by controlled cooling. This can be achieved by any means, e.g., flash or controlled evaporation of water, or even by controlled dilution with colder water, or any combination of these methods. This cooling operation can be carried out either batchwise or continuously, in a single crystallizer or in a plurality of vessels. In any case, the temperature profile should be selected so as to be maintained as closely as possible inside the supersaturated region for terephthalic acid in order to minimize the occlusion of impurities into the reprecipitated crystals. Obviously, any physical treatment of the hot solution before cooling may be applied without departing from the scope of the present invention. For instance, the hot solution may be passed through a bed of charcoal or any resistant absorbent to help in removing any colored contaminant and/or residual metal.

Although the crystallization of terephthalic acid from water has been extensively described and is actually applied on a commercial scale for the separation of terephthalic acid from solutions containing small amounts of p-toluic acid, no such process has been proposed heretofore to remove 4-carboxybenzaldehyde. The reason for this is given in U.S. Pat. No. 3,497,552, viz.: "By subjecting the recovered crystalline terephthalic acid to several (e.g., 3 to 5) recrystallizations, from water, the impurity level may be reduced to less than one percent. However, the number of additional recrystallizations necessary to obtain 99.9 percent pure terephthalic acid are sufficiently great as to make such a purification rate not commercially feasible". (column 3, lines 32–39) Even when only p-toluic acid is present as an impurity, "it is exceedingly difficult to crystallize terephthalic acid free from contamination with p-toluic acid" (U.S. Pat. No. 3,505,398, column 1, lines 33–35), and the patent literature is abundant in describing that much care must be exercized to successfully achieve this operation.

In view of these prior art teachings, it is highly surprising, therefore, that the 4-carboxybenzaldehyde level in terephthalic acid can be quite efficiently reduced from more than about 2% by weight down to the fiber grade by merely resorting to 2 or 3 successive recrystallizations in accordance with the process of the present invention. In fact, it has been discovered that in order to achieve such a purification, it is essential that not only the crystallization of terephthalic acid from water but also the separation and washing thereof from the mother liquor be carried out at a sufficiently high temperature, preferably above about 185° C., more preferably between about 190° and 240° C. and still more preferably between about 200° and 230° C. As a matter of fact, the efficiency of the purification achieved by crystallization is markedly dependent on temperature. Below about 185° C., no efficient separation from 4-carboxybenzaldehyde will take place. On the other hand, at temperatures above about 240° C., the solubility in water of terephthalic acid itself increases so steeply that the proportion thereof which crystallizes upon cooling would become impractically low.

As those skilled in the art will realize, the presence in the mother liquor of substantial amounts of partially-oxidized impurities and of terephthalic acid still dissolved at the relatively high temperatures used for the crystallization requires that the mother liquor be further processed for recycling this dissolved material into the oxidation process wherein crude terephthalic acid is produced. This requirement may pose a problem in cases where the oxidation process does not make use of water as a diluent. For instance, with an oxidation process wherein acetic acid is used, the mother liquor should be treated so as to separate completely the water from the dissolved material to be recycled, and this would bring additional processing costs. By contrast, with water-diluted oxidation systems, the same aqueous mother liquor may be recycled as such, possibly after some simple concentration treatment, if necessary.

Another technical problem for practicing the present purification process may arise from the fact that the separation and washing of terephthalic acid from the mother liquor, in accordance with this invention, must be carried out at least at the same high temperature as used for the crystallization itself. The vapor pressures developed by water in the temperature range of from about 190° to 240° C., where those operations are preferably carried out, amount to between about 12 and 33 atmospheres. These pressures are much higher than those for which conventional equipment for solid-liquid separation have been designed, such as centrifuges or rotary filters. Accordingly, other separation devices, such as hydrocyclones or sedimentation columns, should be provided in commercial practice. By reason of their simple static design and the efficient counter-current washing effected therein, sedimentation columns are preferred.

The present invention will now be further described with reference to the following examples, which are given for a sake of illustration only and should not be considered as limiting the scope of the present invention.

EXAMPLE 1

Into a titanium autoclave are charged 30 g of an impure terephthalic acid sample obtained by oxidation of p-xylene in an aqueous medium and having the following composition, in % by weight:

| terephthalic acid | 94.0% |
|---|---|
| p-toluic acid | 3.7% |
| 4-carboxybenzaldehyde | 2.3% |

To this sample is added 300 g of water. The amount of solid material in this operation is therefore 10 parts (9.4 parts of terephthalic acid) for each 100 parts of water. The resulting slurry is then heated under a nitrogen atmosphere while stirring for 4 hours at 270° C. The resulting solution is then progressively cooled down to 200° C., at a rate of about 0.8° C. per min. with continued stirring.

The resulting slurry is then transferred onto a heated pressure filter by applying nitrogen pressure in the crystallizer. The crystals thus separated are washed by re-slurrying in 10 parts of water and stirring for 1.30 hours at 200° C., i.e., the same temperature as ultimately reached in the crystallization. The washed crystals are then separated by filtration as described above, dried under vacuum at 80° C. and analyzed; p-toluic acid is determined by HPLC and 4-carboxybenzaldehyde by colorimetric analysis. The crystals are shown to contain 2018 ppm of 4-carboxybenzaldehyde and 80 ppm of p-toluic acid.

EXAMPLE 2

The terephthalic acid crystals recovered in the preceding example are submitted to the same purification treatment as applied to the crude sample. In the resulting product, p-toluic acid is no longer detectable, and 4-carboxybenzaldehyde amounts to only 197 ppm.

EXAMPLE 3

The procedure of Example 1 is repeated, except that the hot solution of impure terephthalic acid is cooled down to 220° C. instead of 200° C. After washing and drying as described earlier, the resulting crystals are shown to contain only 509 pm of 4-carboxybenzaldehyde, instead of 2018 ppm as in Example 1. The p-toluic acid content thereof is shown to be 66 ppm.

This example thus illustrates the importance of temperature on the purity of terephthalic acid crystals obtained according to the present invention.

EXAMPLE 4

The terephthalic acid crystals recovered in the preceding example are submitted to the same purification treatment as applied to the crude sample. In the resulting product, 4-carboxybenzaldehyde amounts to 35 ppm.

This example shows that, by the process of the present invention, it is possible to reduce the 4-carboxybenzaldehyde level from about 25,000 ppm down to substantially the fiber-grade requirement by only two crystallization stages.

EXAMPLE 5

Into the same crystallizer as used in the preceding examples, there is charged 60 g of an impure terephthalic acid sample having the following composition, in weight %:

| | |
|---|---|
| terephthalic acid | 93.0% |
| p-toluic acid | 4.6% |
| 4-carboxybenzaldehyde | 2.3% |

To this sample is added the same amount of water as in the preceding examples, so that the amount of solid material in this case amounts to 20 parts (18.6 parts of terephthalic acid) per 100 parts of water. This more concentrated slurry is then treated exactly as described in Example 3. The resulting purified crystals are shown upon analysis to contain 699 ppm of 4-carboxybenzaldehyde and 56 ppm of p-toluic acid, instead of 509 and 66 ppm respectively, as in Example 3. This comparison shows that the beneficial effect of increasing dilution with water, although significant, is much less important than the effect of increasing the temperature of crystallization, as demonstrated by the comparison between the results of Examples 1 and 3.

COMPARATIVE EXAMPLE A

A terephthalic acid sample with substantially the same composition as in the preceding example is recrystallized according to the same procedure, except that cooling is effected down to 160° C. instead of 220° C. The resulting crystals are shown to contain as much as 2708 ppm of 4-carboxybenzaldehyde and 808 ppm of p-toluic acid. The comparison between these figures and the results of the preceding example demonstrate the importance of working at a high temperature for achieving efficiently the purification of terephthalic acid by the process of the present invention.

EXAMPLE 6

An aliquot part of the terephthalic acid crystals recovered in Example 5 is submitted to the same purification treatment as applied to the crude sample. In the resulting product, 4-carboxybenzaldehyde amounted to only 38 ppm, i.e., about the same level as obtained in Example 4. This demonstrates, once again, that the water concentration of the material to be purified is not critical in the recrystallization process of the present invention.

COMPARATIVE EXAMPLE B

Another aliquot part of the crystals recovered in Example 5 is submitted to the same purification treatment as in the preceding example, except that cooling is effected down to 160° C. instead of 220° C. The resulting crystals are shown to contain 105 ppm of 4-carboxybenzaldehyde, i.e., substantially more than obtained in the preceding example.

What is claimed is:

1. A process for the purification to fiber-grade quality of a crude terephthalic acid product contaminated with up to 10% by weight of partially oxidized impurities including p-toluic acid and an amount of 4-carboxybenzaldehyde which is higher than the amount permissible for fiber grade terephthalic acid, comprising the steps of:
    (a) dissolving the crude product in water by heating up to a temperature at least about 5° C. higher than necessary for having the resulting solution saturated with terephthalic acid;
    (b) cooling the resulting solution down to a temperature greater than 185° C. to precipitate purified crystals;
    (c) recovering the purified crystals by solid-liquid separation at a temperature not lower than that used for the precipitation of the purified crystals; and
    (d) washing the recovered crystals by contacting with water at a temperature which is at least as high as the temperature of the recovery step.

2. The process of claim 1, wherein the crude product is dissolved in water at a temperature at least about 5° C. higher than the temperature T given by the formula $T = 57.15 \log [TPA] + 184.9$, where T is the temperature in °C. and [TPA] is the concentration of terephthalic acid present in parts by weight per 100 parts of water.

3. The process of claim 2, wherein the concentration of terephthalic acid is comprised of between about 5 and about 50 parts by weight per 100 parts of water.

4. The process of claim 3, wherein said concentration is comprised between about 10 and 30 parts by weight per 100 parts of water.

5. The process of claim 1, wherein the cooling step, the recovering step and the washing step are performed at a temperature between about 190° C. and 240° C.

6. The process of claim 5, wherein said temperature is between about 200° and 230° C.

7. The process of claim 1, further comprising the steps of dissolving in water the washed crystals of terephthalic acid obtained in step (d) to form a second solution by heating up to a temperature at least about 5° C. higher than necessary for having the second resulting solution saturated with terephthalic acid, cooling said second solution down to a temperature not lower than about 185° C., separating the purified terephthalic acid which crystallizes out and washing the separated crystals with water at a temperature not lower than the cooling temperature for said second solution, whereby fiber-grade terephthalic acid is recovered.

8. A process for the purification of a crude terephthalic acid product contaminated with up to about 5% by weight (50,000 ppm) of p-toluic acid and up to about 2.5% by weight (25,000 ppm) of 4-carboxybenzaldehyde to produce fiber-grade terephthalic acid, which process comprises the steps of:
    (a) dissolving from about 10 to 30 parts by weight of said crude product in 100 parts of water at a temperature between about 247° and 275° C., to produce a first solution;

(b) cooling the resulting first solution down to a temperature between about 190° and 240° C., to precipitate crystals;

(c) recovering the precipitated crystals by solid-liquid separation at the temperature ultimately reached in the colling step;

(d) washing the recovered crystals by contacting with water at the same temperature as in the recovery step;

(e) dissolving from about 10 to 30 parts by weight of the washed crystals in 100 parts of water at a temperature between about 247° and 275° C., to produce a second solution;

(f) recooling the resulting second solution down to a temperature between about 190° and 240° C. to reprecipitate crystals;

(g) recovering the reprecipitated crystals by solid-liquid separation at the temperature ultimately reached in said re-cooling step; and (h) washing the reprecipitated crystals by contacting with water at the same temperature as in the recovery step (g).

9. The process of claim 1, wherein the amount of 4-carboxybenzaldehyde in the crude terephthalic acid is greater than about 2% by weight.

10. The process of claim 9, wherein the amount of 4-carboxybenzaldehyde in the crude terephthalic acid is between about 2 and 2.5% by weight.

11. The process of claim 5, wherein said temperature is greater than about 200° C.